(12) United States Patent
Cao et al.

(10) Patent No.: US 12,130,253 B2
(45) Date of Patent: Oct. 29, 2024

(54) METHOD FOR SELECTIVE DETECTION OF L-TRYPTOPHAN USING FORMALDEHYDE AS MEDIUM

(71) Applicant: CHANGSHA UNIVERSITY OF SCIENCE AND TECHNOLOGY, Changsha (CN)

(72) Inventors: Zhong Cao, Changsha (CN); Junyi He, Changsha (CN); Qin Zhu, Changsha (CN); Chu Liu, Changsha (CN); Saifei Feng, Changsha (CN); Huiying Hu, Changsha (CN); Donghong Yu, Changsha (CN)

(73) Assignee: CHANGSHA UNIVERSITY OF SCIENCE AND TECHNOLOGY, Changsha (CN)

( * ) Notice: Subject to any disclaimer, the term of this patent is extended or adjusted under 35 U.S.C. 154(b) by 902 days.

(21) Appl. No.: 17/271,164

(22) PCT Filed: Aug. 24, 2020

(86) PCT No.: PCT/CN2020/110769
§ 371 (c)(1),
(2) Date: Feb. 24, 2021

(87) PCT Pub. No.: WO2021/103682
PCT Pub. Date: Jun. 3, 2021

(65) Prior Publication Data
US 2022/0065808 A1  Mar. 3, 2022

(30) Foreign Application Priority Data
Nov. 25, 2019 (CN) .......................... 201911169262.X

(51) Int. Cl.
*G01N 27/327* (2006.01)
*C01B 32/174* (2017.01)
*G01N 27/48* (2006.01)

(52) U.S. Cl.
CPC ....... G01N 27/3278 (2013.01); C01B 32/174 (2017.08); G01N 27/48 (2013.01); *C01B 2202/06* (2013.01); *C01B 2202/22* (2013.01)

(58) Field of Classification Search
CPC ............ G01N 27/308; G01N 27/3277; G01N 27/3278; G01N 27/48; G01N 33/6812; C01B 32/174; C01B 2202/06
See application file for complete search history.

(56) References Cited

U.S. PATENT DOCUMENTS

2018/0052134 A1* 2/2018 Kawde .................. G01N 27/48
2018/0164240 A1* 6/2018 Seckler ................ G01N 27/227

FOREIGN PATENT DOCUMENTS

CN   102323305 A   1/2012
CN   106290537 A   1/2017
(Continued)

OTHER PUBLICATIONS

Q. Zhu, Highly sensitive determination of L-tyrosine in pig serum based on ultrathin CuS nanosheets composite electrode, Biosensors and Bioelectronics 2019(140), 111356, p. 1-8. (Year: 2019).*

(Continued)

*Primary Examiner* — C. Sun
(74) *Attorney, Agent, or Firm* — Bayramoglu Law Offices LLC

(57) ABSTRACT

A method for a selective detection of L-tryptophan (L-Trp) using formaldehyde as a medium is disclosed. The method includes preparation of a copper sulfide nanosheets-chitosan/acidified functionalized multi-wall carbon nanotubes (CuS NS—CS/F-MWCNTs) composite material, prepara- (Continued)

tion of a composite film-modified electrode CuS NS—CS/F-MWCNTs/GCE, and a detection of the L-Trp. Since oxidation peaks of L-Trp and L-tyrosine (L-Tyr) overlap and are difficult to separate, the present invention provides a method for a highly selective detection of L-Trp through the Pictet-Spengler reaction of formaldehyde (HCHO) with L-Trp, in which the oxidation peak potential of L-Trp is shifted to 0.82 V and the oxidation peak potential of L-Tyr is 0.63 V, thereby effectively avoiding the interference of L-Tyr. The CuS NS—CS/F-MWCNTs/GCE is applied to detect L-Trp in the formaldehyde medium without any interference from L-Tyr or other amino acids with 50-fold concentrations.

16 Claims, 13 Drawing Sheets

(56) References Cited

FOREIGN PATENT DOCUMENTS

| CN | 108362815 A | 8/2018 |
|---|---|---|
| CN | 110082413 A | 8/2019 |
| CN | 110887881 A | 3/2020 |
| WO | 0242771 A2 | 5/2002 |

OTHER PUBLICATIONS

X. Tang, Electrochemical determination of L-Tryptophan, L-Tyrosine and L-Cysteine using electrospun carbon nanofibers modified electrode, Talanta, 2010(80), p. 2182-86. (Year: 2010).*

X.C. Lu, CuS-MWCNT Based Electrochemical Sensor for Sensitive Detection of Bisphenol A, Russian Journal of Electrochemistry, 2017(53), p. 366-73. (Year: 2017).*

Xu, CN107478685, machine translation. (Year: 2017).*

Cao CN 110082413, machine translation (Year: 2019).*

Zhu Qin, Study on Highly Selective Detection of Amino Acids by Using Ultrastructure Metal Nanocomposite Membranes, A thesis submitted in partial satisfaction of the Requirements for the degree of Master of Science in Chemistry in Changsha University of Science & Technology, Engineering Technology, China Master's Theses Full-Text Database, 2019, pp. 1-73.

Li Yuqing, et al., Graphene Oxide/Triangular Gold Nanoplates/Nafion Composite Modified Electrode Used for Sensitive Detection of L-Tryptophan, Chemical Journal of Chinese Universities, 2018, pp. 636-644, vol. 39, No. 4.

* cited by examiner

METHOD FOR SELECTIVE DETECTION OF L-TRYPTOPHAN USING FORMALDEHYDE AS MEDIUM

CROSS REFERENCE TO THE RELATED APPLICATIONS

This application is the national phase entry of International Application No. PCT/CN2020/110769, filed on Aug. 24, 2020, which is based upon and claims priority to Chinese Patent Application No. 201911169262.X, filed on Nov. 25, 2019, the entire contents of which are incorporated herein by reference.

TECHNICAL FIELD

The present invention belongs to the field of chemical/biological sensing technology, and in particular to a method for a selective detection of L-tryptophan using formaldehyde as a medium.

BACKGROUND

L-tryptophan (L-Trp) is a derivative of alanine and has an indole substituent on the R carbon, which is an important amino acid in protein and a necessary nutrient for human body to establish and maintain positive nitrogen balance. Since L-Trp cannot be synthesized directly by the human body, L-Trp needs to be obtained from food or drug supplement, therefore it is widely used in food industry. Tryptophan is also a precursor of neurotransmitter such as 5-hydroxytryptophan, melatonin, nicotinic acid and serotonin, and it is an indispensable amino acid in the human body. The metabolic disorder of tryptophan will produce some toxic substances, causing schizophrenia, hallucinations, delusions and Alzheimer's disease. Especially, products generated by a strong oxidation reaction of tryptophan may cause some cancers. It is reported that tryptophan is also an indicator for diagnosing early gastric cancer. The measurement of tryptophan content in gastric juice can prompt the diagnosis of early gastric cancer. In addition, an excessive low level of L-Trp in animals will affect the growth and development of the animals. Therefore, it is of great significance to establish a rapid and accurate method for the detection of L-Trp in the field of life sciences.

At present, the detection methods of L-Trp have been reported worldwide, mainly including spectrophotometry, fluorescence spectrometry, ion-exchange chromatography, high-performance liquid chromatography (HPLC), gas chromatography-mass spectrometry (GC-MS), capillary electrophoresis and etcetera. However, instruments used in these methods are cumbersome, expensive and complicated to operate. Using electrochemical sensors for the detection of L-Trp has the advantages of simple operation, low cost, good selectivity and high sensitivity, which has attracted extensive attention of researchers. Naganathan et al. successfully prepared a glassy carbon electrode (GCE) modified with a nanocomposite consisting of moss ball-like cerium-doped ZnO and functionalized multiwalled carbon nanotubes (Ce—ZnO/f-MWCNT) by a low-temperature hydrothermal method. The electrode showed high sensitivity and good linear response to Trp oxidation. Haldorai et al. prepared a flower-like structured nanocomposite electrode consisting of reduced graphene oxide (rGO) and stannic oxide ($SnO_2$) by a hydrothermal method. The electrode had good conductivity and not only showed the ability to quickly transfer electrons, but also showed a good catalytic oxidation ability for Trp. Hasanzadeh et al. prepared $Fe_3O_4$ magnetic nanoparticles/graphene quantum dots ($Fe_3O_4$ MNP-GQDS) composite film-modified electrode, which can be used for the sensitive detection of Trp and the study of Trp kinetic reaction process. The sensor had the functions of reducing oxidation potential and enhancing oxidation current.

However, it is difficult to separate L-Trp and L-tyrosine (L-Tyr) because of their overlapping oxidation peaks, and this problem has not been well solved in the current research on the detection of L-Trp by non-enzymatic sensors, especially the problems such as whether the interference of L-Tyr can be effectively avoided and the highly selective detection of L-Trp can be achieved. Therefore, it is crucial to establish a method for a highly selective detection of L-Trp, which is also an essential trend of the research on selective detection of amino acid in the field of life sciences. On this basis, the present invention provides a method for a selective detection of L-Trp using formaldehyde as a medium. The present invention effectively avoids the interference of L-Tyr through the Pictet-Spengler reaction of formaldehyde (HCHO) and L-Trp, and achieves the objective of the selective detection of L-Trp. Up to now, the electrochemical sensing method for the detection of L-Trp based on the chemical reaction of Trp and formaldehyde has not been reported.

SUMMARY

In order to overcome the deficiencies of the prior art, the present invention provides a method for a highly selective detection of L-tryptophan (L-Trp) using formaldehyde as a medium.

In order to achieve the above objective, the technical solution provided by the present invention is as follows.

The method for the highly selective detection of the L-Trp using formaldehyde as the medium includes the following steps:

(1) preparation of a copper sulfide nanosheets-chitosan/acidified functionalized multi-wall carbon nanotubes (CuS NS—CS/F-MWCNTs) composite material:
  a) preparing surface carboxylated F-MWCNTs by a blending acidification method;
  b) preparing CuS NS;
  c) dissolving the F-MWCNTs prepared in step a) in anhydrous ethanol to form an F-MWCNT solution with a concentration of 0.8-1.2 mg/mL, preferably 1 mg/mL; mixing the CuS NS prepared in step b) with a CS solution having a mass percentage of 0.8-1.2%, preferably 1%, according to a mass/volume ratio of (4.5-5.5) mg: (0.05-0.15) mL, preferably 5 mg: 0.1 mL, and then dissolving in anhydrous ethanol to prepare a CuS NS—CS solution with a CuS concentration of 4.5-5.5 mg/mL, preferably 5 mg/mL;

(2) preparation of a composite film-modified electrode, i.e., CuS NS—CS/F-MWCNTs/GCE: polishing a surface of a glassy carbon electrode, performing an ultrasonic cleaning and an air drying, and performing an ultrasonic dispersion on the F-MWCNT solution to obtain an F-MWCNT dispersed solution, then coating the F-MWCNT dispersed solution on the surface of the glassy carbon electrode dropwise and performing an air drying, to obtain an F-MWCNT-modified glassy carbon electrode; performing an ultrasonic dispersion on the CuS NS—CS solution to obtain a CuS NS—CS homogeneous solution, then coating the CuS NS—CS homogeneous solution on the F-MWCNT-modified glassy carbon electrode dropwise and performing an air drying, to obtain the composite film-modified electrode, i.e., the CuS NS—CS/F-MWCNTs/GCE;

(3) using the CuS NS—CS/F-MWCNTs/GCE as a working electrode, an Ag/AgCl electrode as a reference electrode and a platinum wire electrode as a counter electrode to form a three electrode system; detecting an electrochemical signal of the L-Trp in a formaldehyde-containing buffer solution by differential pulse voltammetry (DPV), in which an oxidation peak potential of the L-Trp is 0.82 V; and testing the L-Trp with different concentrations, drawing a working standard curve, then detecting the L-Trp in a sample to be tested by a standard addition method, in which a concentration of the formaldehyde in the formaldehyde-containing buffer solution is 0.02-0.2 M, the buffer solution is phosphate buffer solution (PBS) with a pH value of 7.0 and a concentration of 0.010-0.10 M, and a preferred concentration of the PBS is 0.010 M.

Preferably, step a) preparing the surface carboxylated F-MWCNTs by the blending acidification method specifically includes the following steps: firstly, mixing F-MWCNTs with a mixed acid of $H_2SO_4$ and $HNO_3$, in which a mass/volume ratio of the F-MWCNTs and the mixed acid of $H_2SO_4$ and $HNO_3$ is (0.15-0.25) g: (25-35) mL, preferably 0.2 g: 30 mL, and a volume ratio of $H_2SO_4$ and $HNO_3$ in the mixed acid of $H_2SO_4$ and $HNO_3$ is (2.5-3.5):1, preferably 3:1; after performing an ultrasonic dispersion, refluxing in an oil bath under stirring at 115-125° C., preferably 120° C., for 2.5-3.5 h, preferably 3 h, to obtain a mixed solution; then diluting the mixed solution with ultrapure water, and centrifuging with a high-speed centrifuge after cooling; finally, after washing with ethanol for three times and centrifuging, drying the product into powder in an electric blast drying oven at 55-65° C., preferably 60° C., to obtain the surface carboxylated F-MWCNTs, and storing for later use.

Preferably, step b) preparing the CuS NS specifically includes the following steps: firstly, adding $CuCl \cdot 2H_2O$ into a container containing a mixture of oleylamine and octylamine, in which a mass/volume ratio of the $CuCl \cdot 2H_2O$ to the mixture of oleylamine and octylamine is (0.15-0.25) g: (25-45) mL, preferably 0.2 g: 40 mL, a volume ratio of the oleylamine and the octylamine in the mixture of oleylamine and octylamine is 1:(1-2); heating in an oil bath to 100° C., and then performing a magnetic stirring under vacuum for 20-60 min, preferably 30 min, to remove water and oxygen; then raising the temperature to 120-140° C., preferably 130° C., and keeping at this temperature with a magnetic stirring for 4.5-6.0 h, preferably 5 h; at the same time, preparing an ultrasonically homogeneous solution of sulfur powder and the mixture of oleylamine and octylamine, in which a mass/volume ratio of the sulfur powder and the mixture of oleylamine and octylamine is (0.1-0.2) g: (3-7) mL, preferably 0.1443 g: 5 mL, a volume ratio of the oleylamine and the octylamine in the mixture of oleylamine and octylamine is 1:(1-2), and preferably 1:1.5; when the solution becomes transparent after heating for 4.5-6.0 h, preferably 5 h, injecting the solution of the sulfur powder and the mixture of oleylamine and octylamine into the solution in the container quickly to obtain a mixed solution, heating the mixture for 8-24 h, preferably 12 h; finally, cooling to room temperature, washing with excess ethanol and centrifuging, and then drying the precipitate into powder in the electric blast drying oven at 55-65° C., preferably 60° C., to obtain the CuS NS, and storing in a refrigerator for later use.

Preferably, a shape of the CuS NS is a hexagon with a side length of 10.46±0.65 nm and a thickness of 5.27±0.74 nm.

Preferably, polishing the surface of the glassy carbon electrode in step (2) is to successively polish the surface of the glassy carbon electrode with 1.0 μm, 0.3 μm and 0.05 μm aluminum oxide powder.

Preferably, a diameter of the glassy carbon electrode in step (2) is 3 mm, 5 μL of the F-MWCNT dispersed solution is coated on the surface of the glassy carbon electrode dropwise and dried, and 5 μL of the CuS NS—CS homogeneous solution is coated on the surface of the F-MWCNT-coated and dried glassy carbon electrode.

Preferably, in step (3), the electrochemical signal of the L-Trp in the formaldehyde-containing buffer solution is detected by the DPV, in which the oxidation peak potential of the L-Trp is 0.82 V, and parameters of the DPV are set as follows: a pulse amplitude is 0.05 V, a pulse width is 0.2 s, a sampling width is 0.02 and a pulse period is 0.5 s. The L-Trp with different concentrations is tested, the working standard curve is drawn. Subsequently, the L-Trp in the sample to be tested is detected by the standard addition method, in which the concentration of the formaldehyde in the formaldehyde-containing buffer solution is 0.02-0.2 M, the buffer solution is the PBS having the pH value of 7.0 and the concentration of 0.010-0.10 M, and the preferred concentration of the PBS is 0.010 M.

In the present invention, the oxidation peak potential during the measurement of the electrochemical signal in the method for selectively detecting the L-Trp using formaldehyde as the medium is 0.82 V, a linear range of the L-Trp is $8.0 \times 10^{-7} - 6.0 \times 10^{-5}$ mol/L, and a lower detection limit is $4.6 \times 10^{-8}$ mol/L. The method of the present invention can be used to construct a sensing platform for selectively detecting L-Trp, and the L-Trp can be separated from L-tyrosine (L-Tyr) when an oxidation peak potential difference thereof ranges from 0.12 to 0.24 V.

The present invention is further described as follows.

The present invention establishes a new method for a selective detection of L-Trp. The intermediate product (2,3,4,9-tetrahydro-1H-pyrido[3,4-b]indole-3-carboxylic acid) is produced by the Pictet-Spengler reaction between the medium formaldehyde (HCHO) and L-Trp, which leads to the positive shift of the oxidation peak potential of L-Trp by 0.19 V, effectively avoiding the interference of the oxidation peak of L-Tyr, thus achieving the highly selective detection of L-Trp. The prepared hexagonal CuS NS with a side length of 10.46±0.65 nm and a thickness of 5.27±0.74 nm is used to construct the CuS NS—CS/F-MWCNTs/GCE. L-Trp is detected based on formaldehyde mediated reaction method. The oxidation peak potential is 0.82 V, the linear range is $8.0 \times 10^{-7} - 6.0 \times 10^{-5}$ mol/L, and the lower detection limit is $4.6 \times 10^{-8}$ mol/L. The method possesses good repeatability, reproducibility and stability, and there is no interference from other amino acids including L-Tyr with 50-fold coexisting concentration. This method is applied to the detection of Trp in pig serums, the results are consistent with those obtained by using the HPLC method, and the measured recovery rate is 94.5%-102.6%. In addition, when the formaldehyde mediated method is used in tests by other sensing interfaces, it is found that the oxidation peak potential of L-Trp shifted positively and can be distinguished from that of L-Tyr, that is, the oxidation peak potential difference between L-Trp and L-Tyr is in the range of 0.12-0.24 V, which fully indicated that this method is expected to construct a sensing platform for the selective detection of L-Trp and possesses a potential application value in the field of bioanalysis.

DETAILED DESCRIPTION OF THE EMBODIMENTS

The reagents used in the examples are analytical pure (AR), and the water used in the experiments is ultrapure water (resistivity≥18.3 MΩ·cm). In the following description, all amino acids are described in abbreviations.

I. Experimental Process

1. Preparation of CuS NS—CS/F-MWCNTs Composite Material

Acidified F-MWCNTs are prepared by the blending acidification method to enable the surface carboxylation. The specific steps are as follows: firstly, 0.2 g of MWCNTs are mixed with 30 mL of a mixed acid of $H_2SO_4$ and $HNO_3$ (a volume ratio of the $H_2SO_4$ and the $HNO_3$ in the mixed acid is 3:1); then the resulting mixture is ultrasonically dispersed at room temperature for 4 h, and then refluxed in a 120° C. oil bath under stirring for 3 h; the mixed solution is diluted with ultrapure water and centrifuged by a high-speed centrifuge after being cooled; finally, the resulting solution is washed with ethanol for three times and centrifuged, then the product is dried into powder in an electric blast drying oven (60° C.) and stored at room temperature for later use.

Preparation of ultra-thin CuS NS: firstly, 0.21 g of $CuCl_2\cdot 2H_2O$, and a mixture consisting of 16 mL of oleylamine (OM) and 24 mL of octylamine (OTA) are added in a 100 mL three-neck flask, filled with nitrogen and heated to 100° C. in an oil bath, and then subjected to a magnetic stirring under vacuum for 30 min to remove water and oxygen; the resulting solution is heated at 130° C. with a magnetic stirring for 5 h until the solution becomes transparent; then the solution is heated at 95° C., and a mixed solution consisting of 0.1443 g of sulfur powder, 2.5 mL of OM and 3.75 mL of OTA is quickly injected into the three-neck flask, and the resulting solution is heated for 12 h; finally the resulting solution is cooled to room temperature, washed with excess ethanol for three times and centrifuged, then the precipitate is dried into powder in the electric blower drying oven (60° C.), and stored in a refrigerator for later use.

The prepared F-MWCNTs are dissolved in anhydrous ethanol to form a 1.0 mg/mL solution. 5 mg of the prepared CuS NS is mixed with 0.1 mL of a 1% (mass percentage) CS solution and dissolved in 0.9 mL of anhydrous ethanol to make the concentration of CuS 5.0 mg/mL. The two solutions are respectively subjected to an ultrasonic oscillation to make them mixed evenly and stored in the refrigerator for later use.

2. Preparation of CuS NS—CS/F-MWCNTs/GCE

Figure 1:
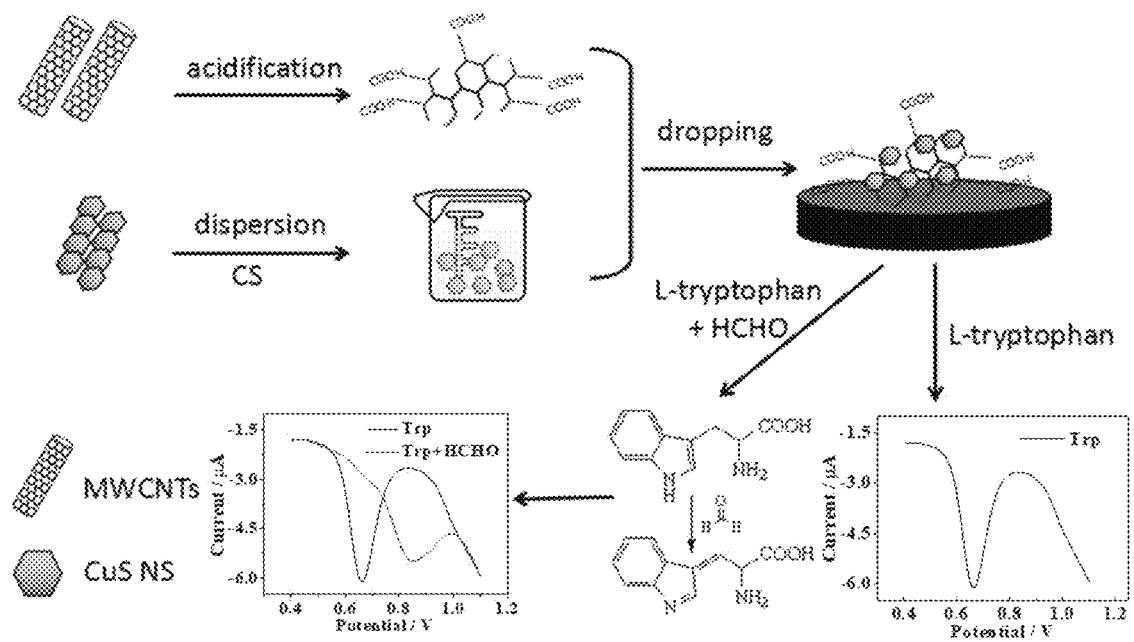
FIG. 1 is a schematic diagram showing the construction of the CuS NS—CS/F-MWCNTs/GCE and the detection method for L-Trp.

The surface of a glassy carbon electrode (having a diameter of 3 mm) is successively polished with 1.0 μm, 0.3 μm and 0.05 μm aluminum oxide powder, subjected to an ultrasonic cleaning in ultrapure water, anhydrous ethanol and ultrapure water respectively for 10 min, and then dried naturally at room temperature. 5 μL of an F-MWCNT dispersed solution after an ultrasonic dispersion is coated on the surface of the glassy carbon electrode dropwise and dried naturally at room temperature; then 5 μL of a CuS NS—CS homogeneous solution after an ultrasonic dispersion is coated dropwise and dried, and stored at 4° C. for later use (as shown in FIG. 1).

3. Electrochemical Detection of L-Trp

The CuS NS—CS/F-MWCNTs/GCE is used as a working electrode, an Ag/AgCl (saturated KCl) electrode is used as a reference electrode and a platinum wire electrode is used as a counter electrode to form a three electrode system. An electrochemical detection is respectively performed on L-Trp and a mixed solution of L-Trp and formaldehyde (the concentration of formaldehyde is 0.02-0.2 M) by an electrochemical workstation, in which the oxidation peak potential of the L-Trp is 0.82 V, the background buffer solution is PBS with a pH value of 7.0 and a concentration of 0.010 mol/L. The parameters of DPV are set as follows: the pulse amplitude is 0.05 V, the pulse width is 0.2 s, the sampling width is 0.02 and the pulse period is 0.5 s. The electrochemical signal of the L-Trp in the formaldehyde-containing buffer solution is detected by the DPV, and L-Trp with different concentrations are tested, then the working standard curve is drawn. The L-Trp in pig serum samples is detected by the standard addition method. The pig serum samples (from 5 live ternary crossbred piglets, weighing 7-15 kg) are provided by Institute of Subtropical Agriculture, Chinese Academy of Sciences (Changsha, China). Five different pig serum samples (50.00 μL) are diluted 100 times in PBS (4.950 mL) with pH=7.0, and then different concentrations of L-Trp are added to the pig serum solutions for determination by the DPV

II. Experimental Results and Analysis

1. Characterization of Materials

Figure 2A:
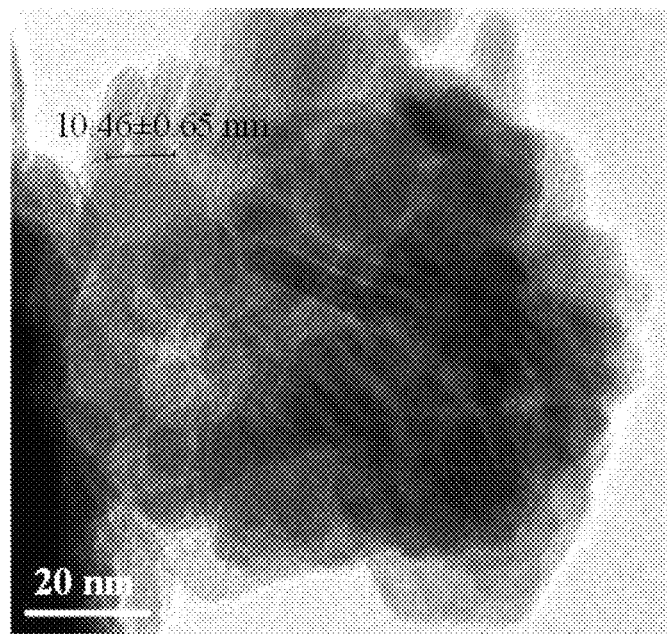
FIG. 2A is a transmission electron microscopy (TEM) diagram showing the morphology of CuS NS material.
Figure 2B:
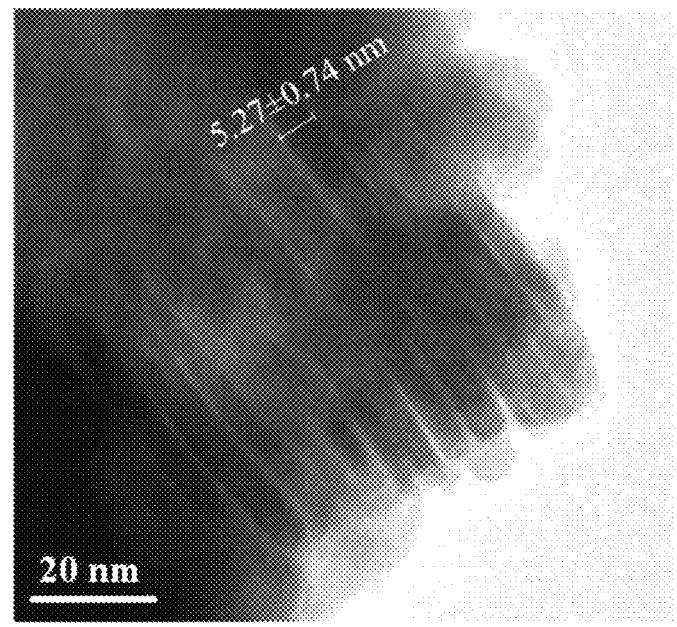
FIG. 2B is a TEM diagram showing the thickness of the CuS NS material.
Figure 2C:
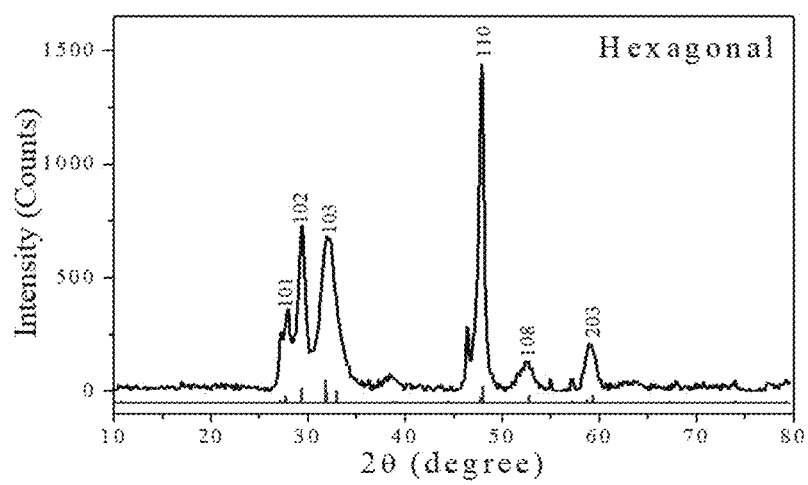
FIG. 2C is an X-ray diffraction (XRD) pattern of CuS NS (hexagonal, PDF: 06-0464, a=b=3.792 Å, C=16.334 Å)

The structure and surface morphology of CuS NS are characterized by TEM. As shown in FIGS. 2A and 2B, CuS are ultra-thin hexagonal nanosheets with a side length of 10.46±0.65 nm and a thickness of 5.27±0.74 nm. FIG. 2C is the XRD pattern of the CuS NS. From the experimental results, it can be concluded that the diffraction peak of the CuS NS corresponds to CuS with a hexagonal structure (PDF: 06-0464), and its lattice constant is a=b=3.792 Å, c=16.334. The results show that the CuS NS prepared by the present invention are nanocrystals with ultrastructure, which play an important role in improving the electrocatalytic performance of the electrode surface.

2. Electrochemical Performance Test

Figure 3A:
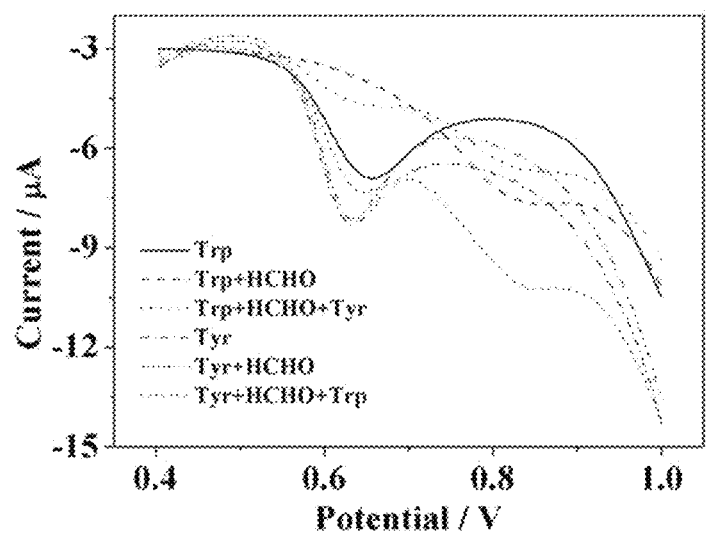
FIG. 3A is a diagram showing DPV curves of the CuS NS—CS/F-MWCNTs/GCE in a mixed solution of L-Trp, HCHO and L-Tyr added in sequence and a mixed solution of L-Tyr, HCHO and L-Trp added in sequence, respectively.
Figure 3B:
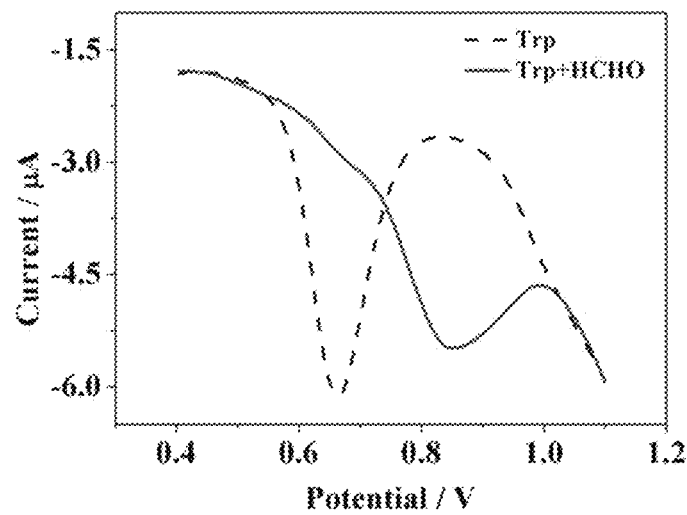
FIG. 3B is a diagram showing DPV curves of the electrode in an L-Trp solution and an L-Trp+HCHO solution, in which concentrations of the L-Trp and the L-Tyr are both $4.0 \times 10^{-5}$ mol/L.

The DPV behaviors of the CuS NS—CS/F-MWCNTs/GCE in a mixed solution of L-Trp ($4.0\times10^{-5}$ mol/L), HCHO and L-Tyr ($4.0\times10^{-5}$ mol/L) added in sequence and a mixed solution of L-Tyr ($4.0\times10^{-5}$ mol/L), HCHO and L-Trp ($4.0\times10^{-5}$ mol/L) added in sequence are investigated (as shown in FIGS. 3A-B). It can be seen from FIG. 3A that the composite electrode has obvious electrochemical signal response to Trp at the potential of 0.632 V. After the addition of formaldehyde, the oxidation peak position of Trp changes to 0.816 V, indicating that the oxidation peak potential of Trp increases after the addition of formaldehyde, which makes it more difficult for oxidation. In order to verify that the method of adding formaldehyde does not change the electrochemical reaction signal of Tyr, L-Tyr is continued to be added at an equal concentration in this experiment. The experimental results show that the peak potentials of Tyr and Trp are separated obviously. In order to further verify the method, Tyr and formaldehyde are added in the experiment. It can be seen from the figure that the oxidation peak potential of Tyr does not change after adding formaldehyde, indicating that formaldehyde in the solution has no effect on the detection of Tyr. When Trp is added, the peak potential of Trp moves from 0.63 to 0.8 V due to the presence of formaldehyde in the solution, and it can be seen from FIG. 3B that the addition of formaldehyde increases the peak potential of the electrochemical signal of Trp, indicating that this method can selectively detect Trp.

3. Selection of Optimal Aldehyde as Medium

Figure 4A:
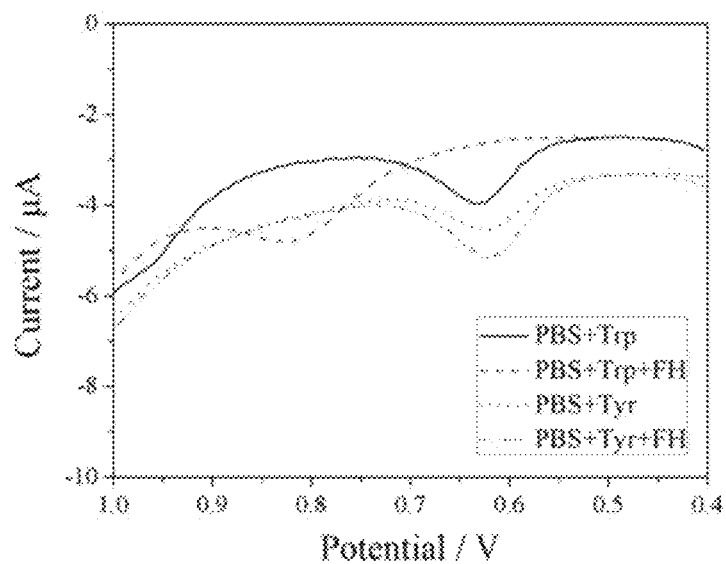
FIG. 4A is a diagram showing DPV curves of the CuS NS—CS/F-MWCNTs/GCE in PBS containing L-Trp and formaldehyde (FH) and PBS containing L-Tyr and FH, in which the concentrations of the L-Trp and the L-Tyr are both $4.0 \times 10^{-5}$ mol/L, the concentration of the FH is 0.131 mol/L, and the concentration of the PBS is 0.010 mol/L (pH=7.0)
Figure 4B:
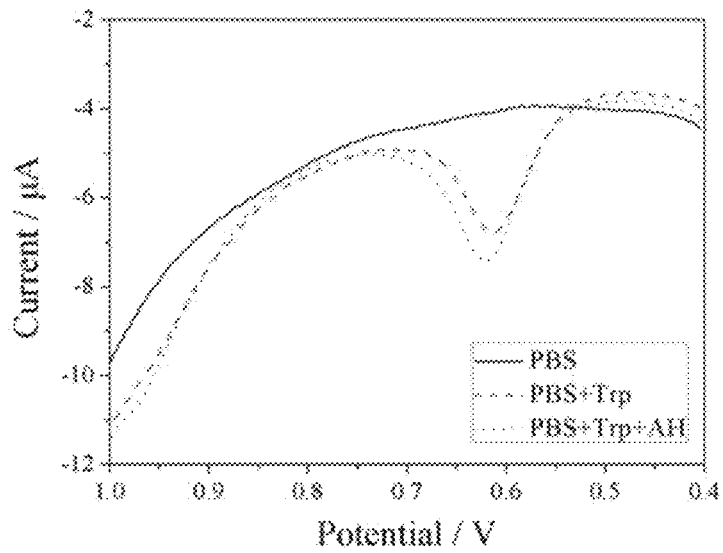
FIG. 4B is a diagram showing DPV curves of the CuS NS—CS/F-MWCNTs/GCE in PBS containing L-Trp and acetaldehyde (AH) and PBS containing L-Tyr and AH, in which the concentrations of the L-Trp and the L-Tyr are both $4.0 \times 10^{-5}$ mol/L, the concentration of the AH is 0.131 mol/L, and the concentration of the PBS is 0.010 mol/L (pH=7.0)
Figure 4C:
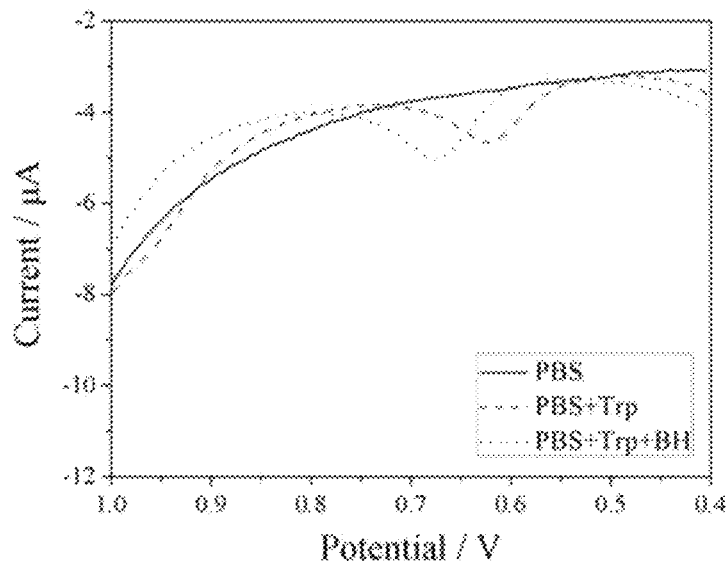
FIG. 4C is a diagram showing DPV curves of the CuS NS—CS/F-MWCNTs/GCE in PBS containing L-Trp and butyraldehyde (BH) and PBS containing L-Tyr and BH, in which the concentrations of the L-Trp and the L-Tyr are both $4.0 \times 10^{-5}$ mol/L, the concentration of the BH is 0.131 mol/L, and the concentration of the PBS is 0.010 mol/L (pH=7.0)
Figure 4D:
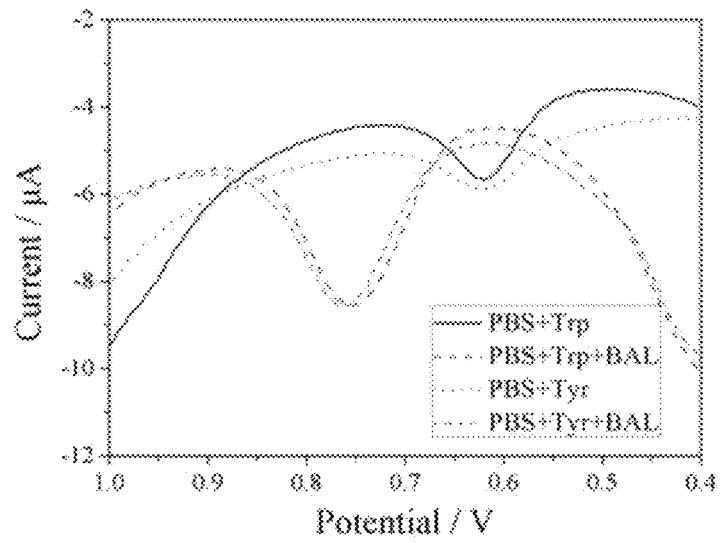
FIG. 4D is a diagram showing DPV curves of the CuS NS—CS/F-MWCNTs/GCE in PBS containing L-Trp and benzaldehyde (BAL) and PBS containing L-Tyr and BAL, in which the concentrations of the L-Trp and the L-Tyr are both $4.0 \times 10^{-5}$ mol/L, the concentration of the BAL is 0.131 mol/L, and the concentration of the PBS is 0.010 mol/L (pH=7.0)
Figure 4E:
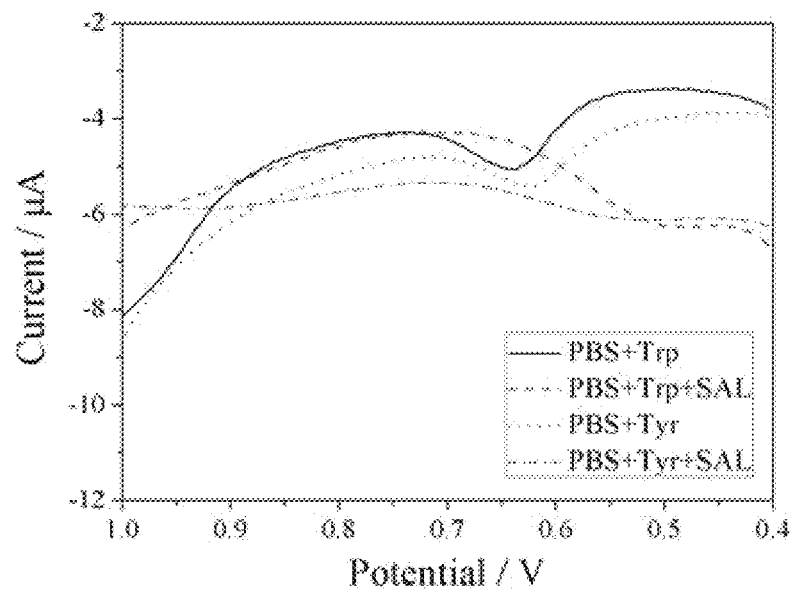
FIG. 4E is a diagram showing DPV curves of the CuS NS—CS/F-MWCNTs/GCE in PBS containing L-Trp and salicylaldehyde (SAL) and PBS containing L-Tyr and SAL, in which the concentrations of the L-Trp and the L-Tyr are both $4.0 \times 10^{-5}$ mol/L, the concentration of the SAL is 0.131 mol/L, and the concentration of the PBS is 0.010 mol/L (pH=7.0)
Figure 4F:
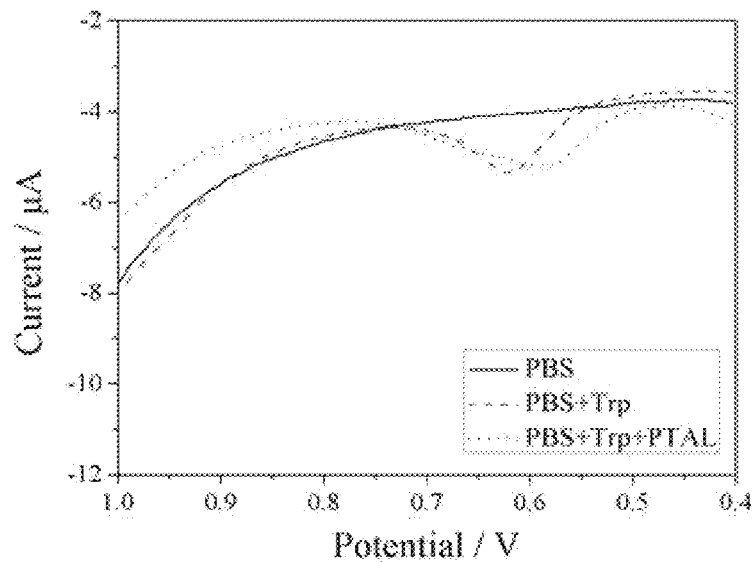
FIG. 4F is a diagram showing DPV curves of the CuS NS—CS/F-MWCNTs/GCE in PBS containing L-Trp and p-tolualdehyde (PTAL) and PBS containing L-Tyr and PTAL, in which the concentrations of the L-Trp and the L-Tyr are both $4.0 \times 10^{-5}$ mol/L, the concentration of the PTAL is 0.131 mol/L, and the concentration of the PBS is 0.010 mol/L (pH=7.0)
Figure 4G:
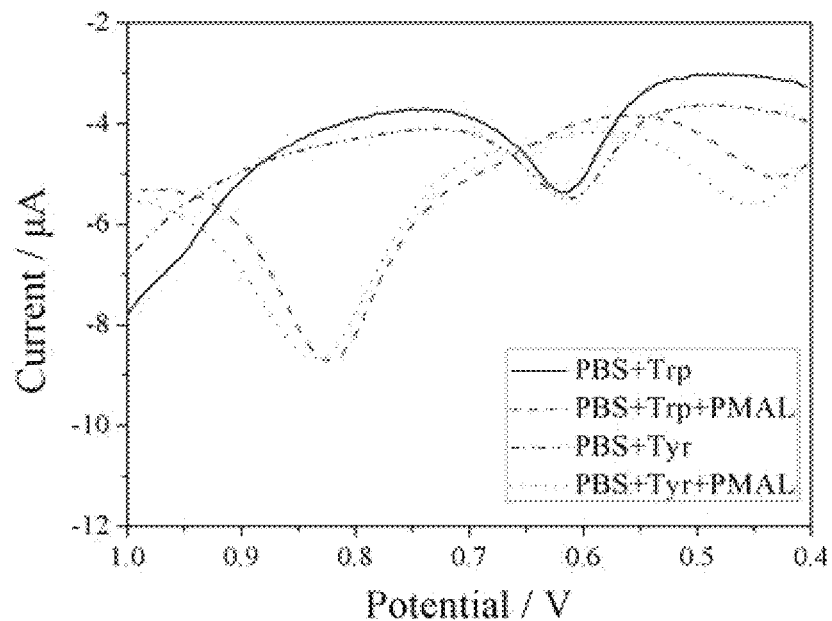
FIG. 4G is a diagram showing DPV curves of the CuS NS—CS/F-MWCNTs/GCE in PBS containing L-Trp and p-methoxybenzaldehyde (PMAL) and PBS containing L-Tyr and PMAL, in which the concentrations of the L-Trp and the L-Tyr are both $4.0 \times 10^{-5}$ mol/L, the concentration of the PMAL is 0.131 mol/L, and the concentration of the PBS is 0.010 mol/L (pH=7.0)
Figure 4H:
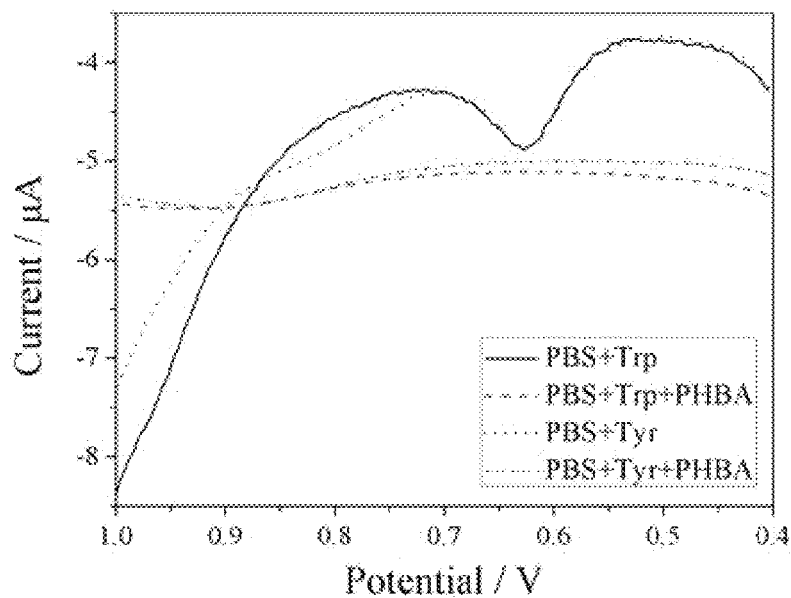
FIG. 4H is a diagram showing DPV curves of the CuS NS—CS/F-MWCNTs/GCE in PBS containing L-Trp and p-hydroxybenzaldehyde (PHBA) and PBS containing L-Tyr and PHBA, in which the concentrations of the L-Trp and the L-Tyr are both $4.0 \times 10^{-5}$ mol/L, the concentration of the PHBA is 0.131 mol/L, and the concentration of the PBS is 0.010 mol/L (pH=7.0)

The DPV is used to test the effect of different aldehydes (0.131 M) added in a 0.010 M PBS solution containing $4.0\times10^{-5}$ M L-Trp on the peak potential of the L-Trp. The results are shown in FIGS. 4A-H. Formaldehyde (FH) has a great effect on the oxidation peak potential of Trp, with the peak potential shifted to the left and the potential difference ΔE=0.184 V (FIG. 4A); acetaldehyde (AH) has no effect on the oxidation peak potential of Trp (FIG. 4B); butyraldehyde (BH) has little effect on the oxidation peak potential of Trp, with the potential difference ΔE=0.052 V (FIG. 4C); benzaldehyde (BAL) has a great effect on the oxidation peak potential of Trp, with the peak potential shifted to the left and the potential difference ΔE=0.136 V (FIG. 4D); salicylaldehyde (SAL) has a great effect on the oxidation peak potential of Trp, with the peak potential shifted to the right and the potential difference ΔE=0.120 V (FIG. 4E); p-methylbenzaldehyde (PTAL) has a slight effect on the oxidation peak potential of Trp, with the peak potential shifted to the right and the potential difference ΔE=0.032 V (FIG. 4F); p-methoxybenzaldehyde (PMAL) has a great effect on the oxidation peak potential of Trp, with the peak potential shifted to the left and the potential difference ΔE=0.208 V (FIG. 4G); p-hydroxybenzaldehyde (PHBA) has a great effect on the oxidation peak potential of Trp, with the peak potential shifted to the right and the potential difference ΔE=0.292 V (FIG. 4H). The above results show that FH, BAL, SAL, PMAL and PHBA each have a great effect on the oxidation peak potential of Trp.

In order to further verify whether these aldehydes also have effects on Tyr, the CuS NS—CS/F-MWCNTs/GCE is used in a 0.010 M PBS mixed solution containing $4.0\times10^{-5}$ M Tyr respectively added with 0.131 M FH, BAL, SAL, PMAL and PHBA to detect the effects on the peak potential of Tyr. The results are shown in FIGS. 4A, 4D, 4E, 4G and 4H. The FH has no effect on the peak potential of Tyr, while the BAL, SAL, PMAL and PHBA all have effects on the peak potentials of L-Trp and L-Tyr. The effects of these four aldehydes on the peak potentials of the two amino acids are the same, indicating that BAL, SAL, PMAL and PHBA cannot separate the oxidation peaks of Trp and Tyr. Therefore, formaldehyde is the optimal medium to separate the oxidation peaks of Trp and Tyr.

4. Effect of pH Value on Electrochemical Behavior of L-Trp

Figure 5A:
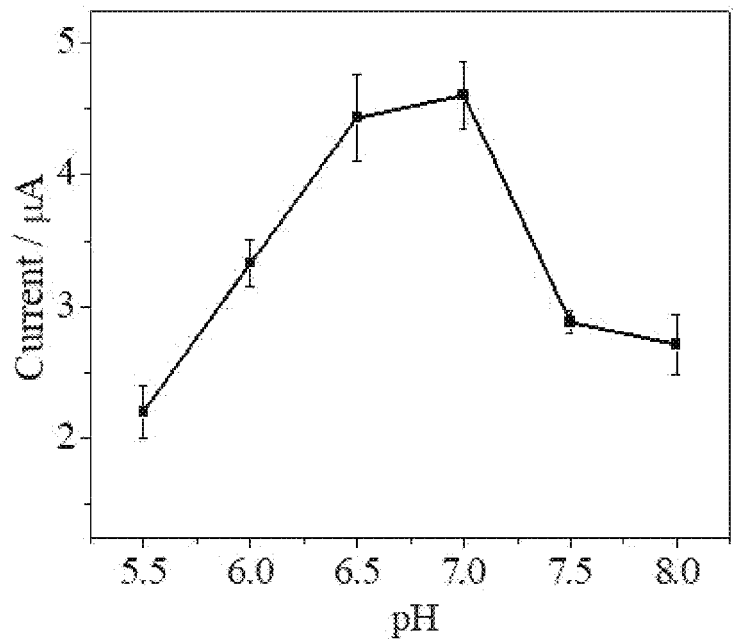
FIG. 5A is a diagram showing curves of the relationship between the oxidation peak current of L-Trp and pH value.
Figure 5B:
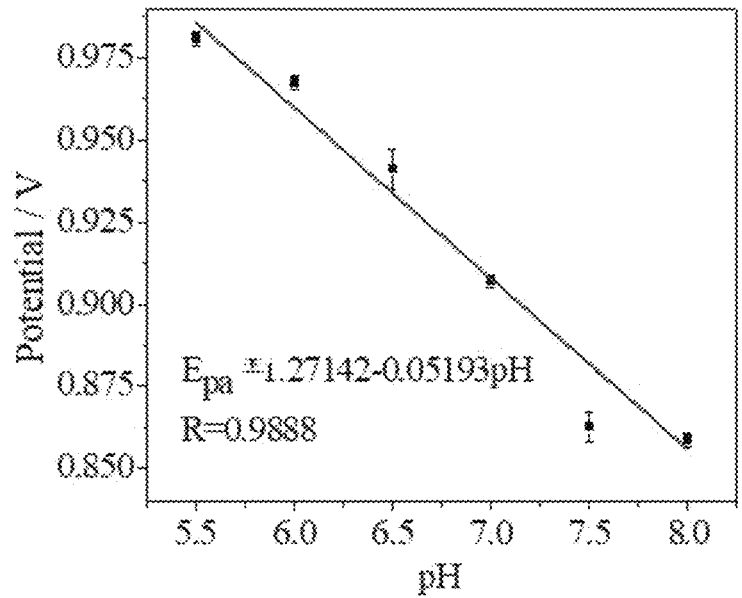
FIG. 5B is a diagram showing curves of the relationship between the oxidation peak potential of L-Trp and pH value.

The pH value of buffer solution is an important factor affecting the oxidation reaction of L-Trp on the electrode surface. The effect of PBS (0.010 mol/L) with a pH ranging from 5.5 to 8.0 on the peak current and peak potential of L-Trp ($4.0\times10^{-5}$ mol/L) is detected by the DPV using the CuS NS—CS/F-MWCNTs/GCE. The change of oxidation peak current of L-Trp with pH value is shown in FIG. 5A. It can be seen from FIG. 5A that when pH is less than 7.0, the peak current increases gradually as the pH increases; when pH is equal to 7.0, the peak current reaches the maximum; when pH is greater than 7.0, the peak current decreases gradually as the pH increases. Therefore, the PBS with pH=7.0 is optimal for the detection of L-Trp. It can be seen from the peak potential curve in FIG. 5B that the peak potential of L-Trp has a linear relationship with pH value, indicating that there is a proton and electron transfer process in the electrode reaction of L-Trp. The linear fitting equation is $E_{pa}=1.27142-0.05193$ pH, and the linear correlation coefficient is R=0.9888. According to Nernst equation: Ep=Eo+0.05916 (m/n) pH (m is the number of protons transferred by the reaction, n is the number of electrons transferred), m=0.8778n, i.e. m≈n, can be calculated, indicating that L-Trp is isoelectron and isoproton transfer at the interface of the modified electrode.

Figure 6:
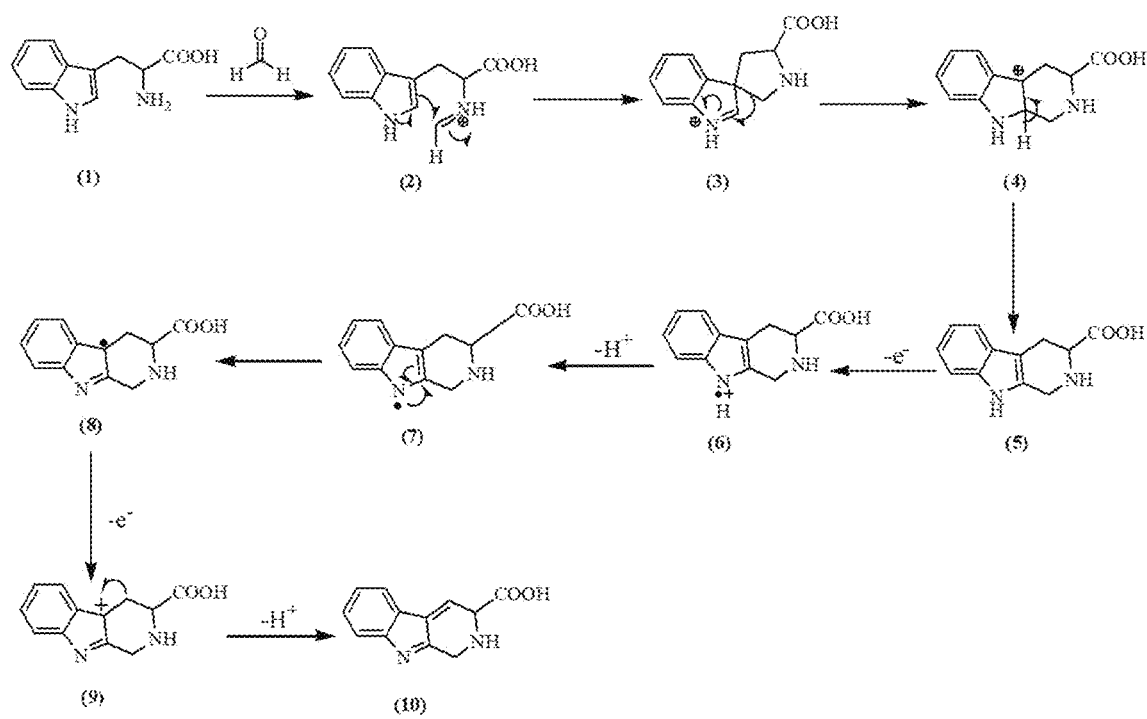
FIG. 6 is a diagram showing the oxidation mechanism of the L-Trp on the CuS NS—CS/F-MWCNTs/GCE after reacting with formaldehyde.

5. Mechanism of L-Trp after Reacting with Formaldehyde by Electrochemical Detection Due to the overlapping oxidation peaks of L-Trp and L-Tyr, it is difficult to separate them. In order to avoid the interference of L-Tyr, formaldehyde is added. The Pictet-Spengler reaction can occur between formaldehyde and L-Trp (1) to condense and dehydrate the β-aromatic ethylamine on L-Trp to form imine (2) (Schiff base). Then the imine cation is isomerized to carbocation, and attacks 3 site of the indole to form an intermediate (3). This reaction has high activity. At the same time, PBS in the solution system provides hydrogen ions to promote the reaction, and finally electrophilic aromatic substitution of aromatic ring is carried out to obtain an intermidiate (4), and cyclization is performed to obtain 2,3,4,9-tetrahydro-1H-pyrido[3,4-b]indole-3-carboxylic acid (5). The product (5) is oxidized on the CuS NS—CS/F-MWCNTs/GCE to lose one electron and obtain a positively charged radical (6). After deprotonation, an intermediate (7) is obtained, and then 4-radical-2,3,4,4a-tetrahydro-1H-pyrido[3,4-b]indole-3-carboxylic acid (8) is formed by intramolecular rearrangement. Through further oxidation, it loses an electron and produces a positive ion (9). After deprotonation, the final 2,3-dihydro-1H-pyrido[3, 4-b]indole-3-carboxylic acid (10) is produced (FIG. 6).

Figure 7:
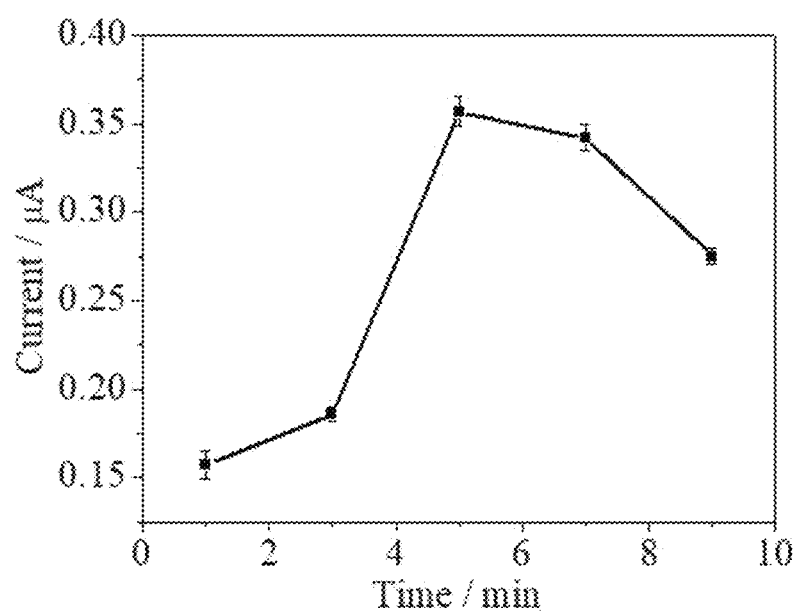
FIG. 7 is a diagram showing the relationship between the oxidation peak current of L-Trp and the reaction time with formaldehyde.

6. Effect of Reaction Time with Formaldehyde on Electrochemical Behavior of L-Trp An oxidation reaction occurs between formaldehyde and Trp in buffer solution. The change of peak current of L-Trp ($4.0\times10^{-6}$ mol/L) on the CuS NS—CS/F-MWCNTs/GCE is investigated by the DPV in PBS (0.010 mol/L) with the optimal pH=7.0 after the reaction of formaldehyde and Trp for different time (FIG. 7). 10 μL of a 37% formaldehyde solution (0.026 mol/L) is added. The results are shown in FIG. 7, when the reaction time of formaldehyde and Trp is within 1-5 min, the shifted peak current signal gradually increases, and when the reaction time is more than 5 min, the shifted peak current signal of L-Trp gradually decreases. Therefore, 5 min is the best reaction time to make formaldehyde react with L-Trp sufficiently and avoid the interference of L-Tyr on the detection of L-Trp.

7. Linear Range and Detection Limit

Figure 8A:
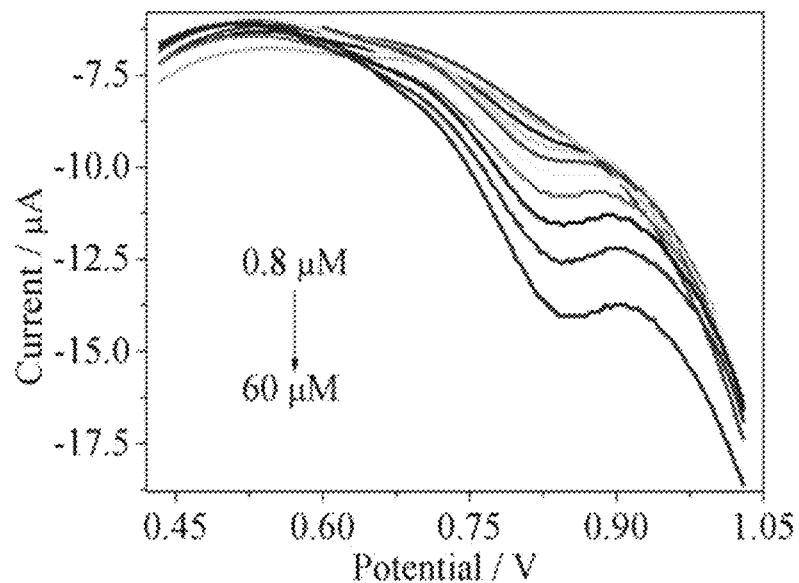
FIG. 8A is a diagram showing DPV curves of the CuS NS—CS/F-MWCNTs/GCE in different concentrations of L-Trp.
Figure 8B:
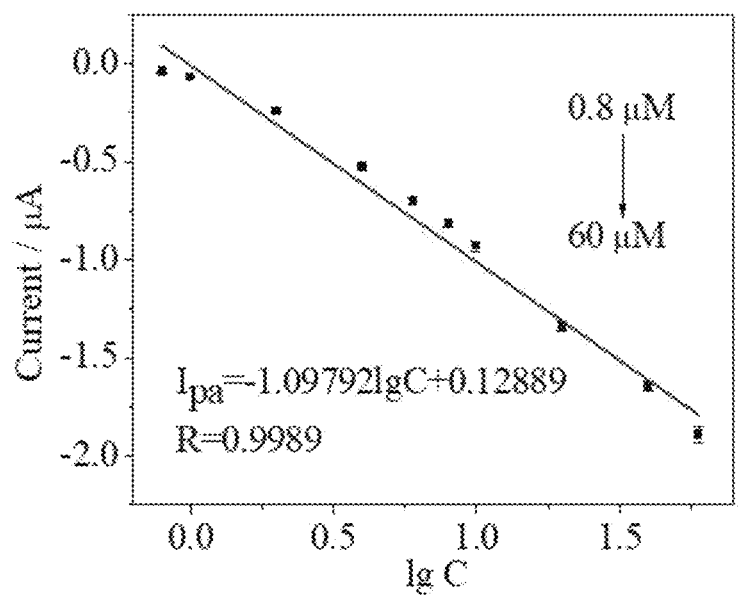
FIG. 8B is a diagram showing the linear relationship between the oxidation peak current and the concentration of L-Trp.

A series of L-Trp standard solutions with different concentrations are prepared. Under the optimal pH value of buffer solution, the CuS NS—CS/F-MWCNTs/GCE is used to detect L-Trp with different concentrations in the formaldehyde solution by the DPV. The oxidation peak potential of L-Trp is 0.82 V. As shown in FIGS. 8A-B, the oxidation peak current of L-Trp has a good linear relationship with its concentration. The concentration range is $8.0\times10^{-7}$-$6.0\times10^{-5}$ mol/L, the linear fitting equation is $I_{pa}=-1.09792$ lgC+0.12889, the linear correlation coefficient is R=0.9989, and the lower detection limit is $4.6\times10^{-1}$ mol/L (S/N=3).

8. Reproducibility, Repeatability and Stability of Electrode

Six modified electrodes are prepared in the same batch under the same conditions to detect the $8.0\times10^{-6}$ mol/L L-Trp solution in formaldehyde medium, respectively. The relative standard deviation of the measured current is 4.89%, indicating that the modified electrode has good reproducibility. The same CuS NS—CS/F-MWCNTs modified electrode is used to detect the $8.0\times10^{-6}$ mol/L L-Trp solution in formaldehyde medium, and the measurement is performed for 6 times continuously. The relative standard deviation of the current is 4.00%, indicating that the modified electrode has good repeatability. In addition, the stability of the modified electrode is investigated. The same modified electrode is used to detect L-Trp in formaldehyde solution at an interval of 48 h under the optimal pH condition and is stored at room temperature when not in use. The results show that after 20 days, the response signal of the modified electrode to L-Trp is 94.9% of that at the beginning. Therefore, the modified electrode has good stability for the detection of L-Trp in formaldehyde medium.

9. Anti-Interference Test

Figure 9:
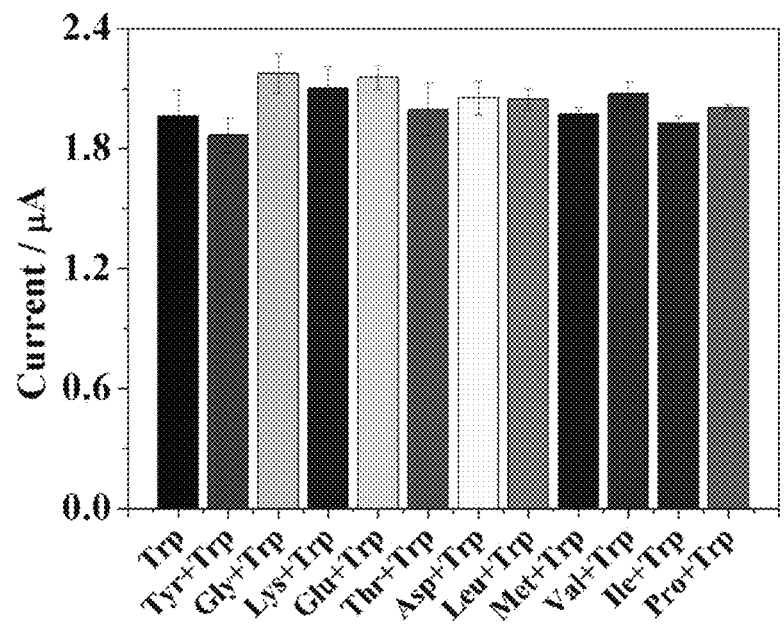
FIG. 9 is a diagram showing the effect of interfering substances on the detection of L-Trp in formaldehyde medium.
Figure 10A:
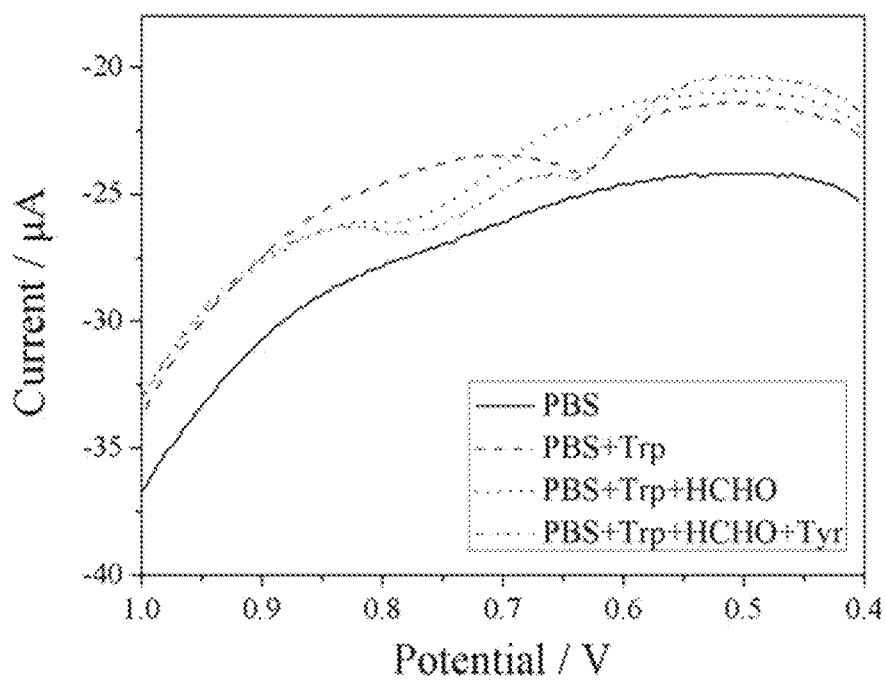
FIG. 10A is a diagram showing DPV curves of GO/F-MWCNTs/Nafion/GCE in PBS, PBS containing L-Trp, PBS containing L-Trp+formaldehyde and PBS containing L-Trp+formaldehyde+L-Tyr, respectively, in which the concentrations of the L-Trp and the L-Tyr are both $4.0 \times 10^{-5}$ mol/L, the concentrations of the various aldehydes are both 0.131 mol/L, and the concentration of the PBS is 0.010 mol/L (pH=7.0)
Figure 10B:
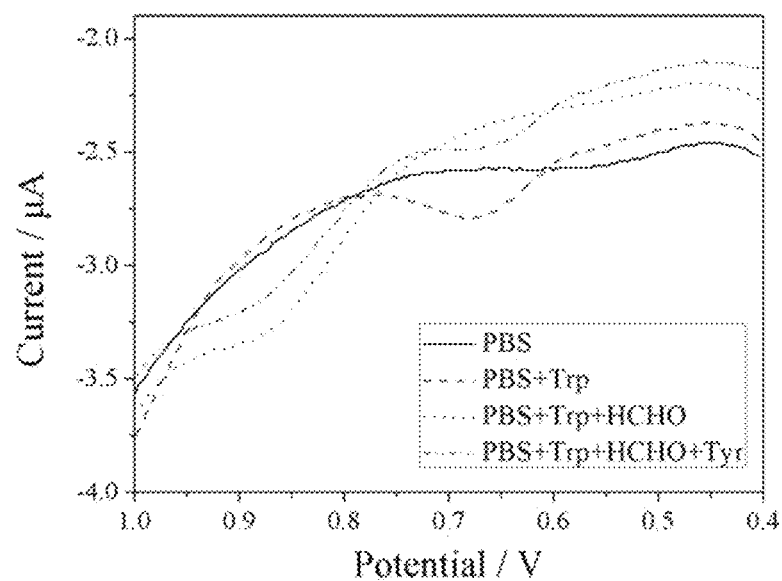
FIG. 10B is a diagram showing DPV curves of 3D Pt—Cu/CNDs/GQDs/GCE in PBS, PBS containing L-Trp, PBS containing L-Trp+formaldehyde and PBS containing L-Trp+formaldehyde+L-Tyr, respectively, in which the concentrations of the L-Trp and the L-Tyr are both $4.0 \times 10^{-5}$ mol/L, the concentrations of the various aldehydes are both 0.131 mol/L, and the concentration of the PBS is 0.010 mol/L (pH=7.0)
Figure 10C:
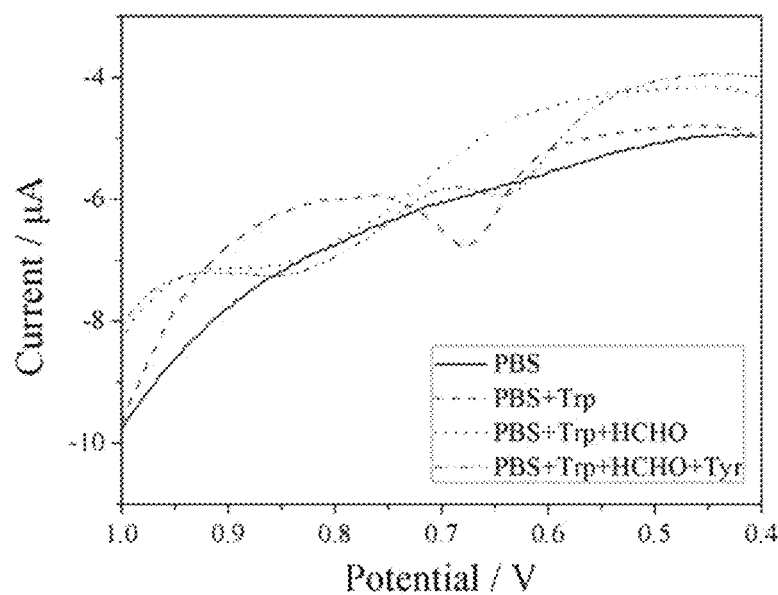
FIG. 10C is a diagram showing DPV curves of $Fe_3O_4$—$SiO_2$/AB-GO/GCE in PBS, PBS containing L-Trp, PBS containing L-Trp+formaldehyde and PBS containing L-Trp+formaldehyde+L-Tyr, respectively, in which the concentrations of the L-Trp and the L-Tyr are both $4.0 \times 10^{-5}$ mol/L, the concentrations of the various aldehydes are both 0.131 mol/L, and the concentration of the PBS is 0.010 mol/L (pH=7.0)
Figure 10D:
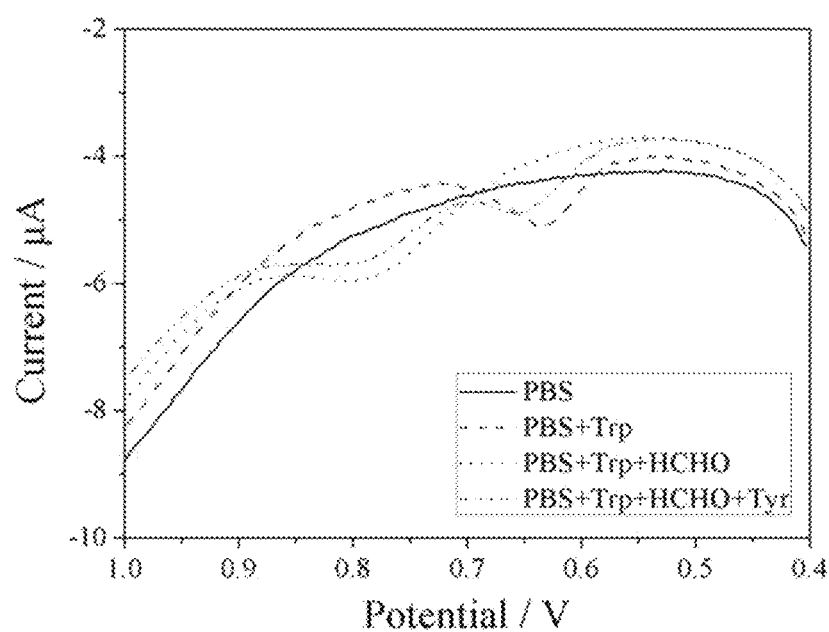
FIG. 10D is a diagram showing DPV curves of Ce@$In_2O_3$/F-MWCNTs/GCE in PBS, PBS containing L-Trp, PBS containing L-Trp+formaldehyde and PBS containing L-Trp+formaldehyde+L-Tyr, respectively, in which the concentrations of the L-Trp and the L-Tyr are both $4.0 \times 10^{-5}$ mol/L, the concentrations of the various aldehydes are both 0.131 mol/L, and the concentration of the PBS is 0.010 mol/L (pH=7.0).

The effect of other amino acids on the oxidation peak current of L-Trp is investigated when using this method to detect L-Trp. The three electrode system that uses PBS (0.010 mol/L) having a pH of 7.0 as the base solution is used to detect L-Trp ($2.0 \times 10^{-6}$) in the presence of other amino acids. The results are as shown in FIG. 9. After adding 50-fold L-glycine (L-Gly), L-lysine (L-Lys), L-glutamic acid (L-Glu), L-threonine (L-Thr), L-aspartic acid (L-Asp), L-leucine (L-Leu), L-methionine (L-Met), L-valine (L-Val), L-isoleucine (L-Ile), L-proline (L-Pro) and L-Tyr, the peak current does not change significantly, indicating that the CuS NS—CS/F-MWCNTs/GCE has a good selectivity for L-Trp.

10. Detection and Recovery Rate Determination of Actual Samples

The application of the CuS NS—CS/F-MWCNTs/GCE in the determination of L-Trp in actual samples (serum) using formaldehyde as a medium is investigated. During detection, the serum sample is diluted 100 times with 0.010 mol/L PBS (pH=7.0), and the experiment is repeated 5 times under the optimal experimental conditions. The results are compared with those obtained by the HPLC method. The detection results are shown in Table 1. It can be seen from Table 1 that the detection results obtained by the two methods are relatively consistent. When using the standard addition method for determination, that is, different concentrations of L-Trp are added to the buffer solution containing serum to perform detection and recovery rate calculation by this method, the measured recovery rate is 94.5-102.6%, indicating that this method has high accuracy and precision for detecting Trp, and can be used for the detection of L-Trp in actual samples.

TABLE 1

Detection and recovery rate of L-Trp in actual samples

| Sample | HPLC (μmoL/L) | Modified electrode (μmoL/L) | RE (%) | Spiked (μmoL/L) | Found (μmoL/L) | Recovery rate (%) | RSD (%) |
| --- | --- | --- | --- | --- | --- | --- | --- |
| Serum 1 | 0.6476 | 0.6153 | 5.0 | 0.9000 | 1.5094 | 95.7 | 2.8 |
| Serum 2 | 0.4157 | 0.4331 | 4.1 | 1.0000 | 1.4333 | 101.8 | 2.1 |
| Serum 3 | 0.3037 | 0.3136 | 3.3 | 1.2000 | 1.5353 | 102.6 | 5.0 |
| Serum 4 | 0.3375 | 0.3414 | 1.2 | 1.3000 | 1.6376 | 100.0 | 2.9 |
| Serum 5 | 0.4372 | 0.4415 | 1.0 | 1.5000 | 1.8548 | 94.5 | 2.3 |

11. Electrochemical Detection of Different Sensing Interfaces Based on Formaldehyde Mediated Reaction The DPV is used to perform a detection of a mixed solution of L-Trp and L-Tyr based on formaldehyde mediated reaction by several different sensing interfaces, such as GO/F-MWCNTs/Nafion/GCE (A), 3D Pt—Cu/CNDs/GQDs/GCE (B), Fe$_3$O$_4$—SiO$_2$/AB-GO/GCE (C), and Ce@In$_2$O$_3$/F-MWCNTs/GCE (D) (FIGS. 10A-D). The results show that the electrochemical sensor that responds to both Trp and Tyr can separate the oxidation peaks of L-Trp and L-Tyr in a mixed solution containing Trp, formaldehyde and Tyr, and the peak potential difference is 0.136 V, 0.188 V, 0.144 V and 0.148 V, respectively, which effectively avoids the interference of L-Tyr on the detection of L-Trp.

In conclusion, the present invention establishes a novel method for a highly selective detection of L-Trp on the basis of the Pictet-Spengler reaction between L-Trp and formaldehyde that produces the intermediate product 2,3,4,9-tetrahydro-1H-pyrido[3,4-b]indole-3-carboxylic acid. Using HCHO as a medium, the oxidation peak potential of L-Trp shifts. Compared with the oxidation peak potential of L-Tyr, the difference of oxidation peak potentials between L-Trp and L-Tyr is 0.12-0.24 V, which effectively avoids the interference of L-Tyr and realizes the highly selective detection of L-Trp. The CuS NS—CS/F-MWCNTs composite electrode and other sensing electrodes are tested by the DPV, which all can achieve sensitive and selective detection of L-Trp after reacting with formaldehyde without interference of L-Tyr or other amino acids, indicating that this method can be used to construct a sensing detection platform for the highly selective detection of L-Trp, thus possessing important application value in the field of life sciences.

What is claimed is:

1. A method for a selective detection of L-tryptophan (L-Trp) using formaldehyde as a medium, comprising the following steps:

(1) a preparation of a copper sulfide nanosheets-chitosan/acidified functionalized multi-wall carbon nanotubes (CuS NS—CS/F-MWCNTs) composite material:
   a) preparing surface carboxylated F-MWCNTs by a blending acidification method;
   b) preparing CuS NS;
   c) dissolving the surface carboxylated F-MWCNTs prepared in step a) in anhydrous ethanol to form an F-MWCNT solution with a concentration of 0.8-1.2 mg/mL, mixing the CuS NS prepared in step b) with a CS solution to obtain a first mixture, wherein the CS solution has a mass percentage of 0.8-1.2%, and a mass/volume ratio of the CuS NS and the CS solution is (4.5-5.5) mg: (0.05-0.15) mL, and then dissolving the first mixture in anhydrous ethanol to prepare a CuS NS—CS solution with a CuS concentration of 4.5-5.5 mg/mL;

(2) a preparation of a composite film-modified electrode CuS NS—CS/F-MWCNTs/GCE: polishing a surface of a glassy carbon electrode to obtain a polished surface of the glassy carbon electrode, performing an ultrasonic cleaning and a first air drying on the polished surface of the glassy carbon electrode, and performing a first ultrasonic dispersion on the F-MWCNT solution to obtain an F-MWCNT dispersed solution, then coating the F-MWCNT dispersed solution on the polished surface of the glassy carbon electrode dropwise to obtain a first processed electrode and performing a second air drying on the first processed electrode, to obtain an F-MWCNT-modified glassy carbon electrode: performing a second ultrasonic dispersion on the CuS NS—CS solution to obtain a CuS NS—CS homogeneous solution, then coating the CuS NS—CS homogeneous solution on the F-MWCNT-modified glassy carbon electrode to obtain a second processed electrode and performing a third air drying on the second processed electrode, to obtain the composite film-modified electrode CuS NS—CS/F-MWCNTs/GCE;

(3) reacting L-Trp with formaldehyde by adding a sample containing L-Trp to a formaldehyde-containing buffer solution; using the composite film-modified electrode CuS NS—CS/F-MWCNTs/GCE as a working electrode, an Ag/AgCl electrode as a reference electrode and a platinum wire electrode as a counter electrode to form a three electrode system, detecting an electrochemical signal of the L-Trp in the formaldehyde-containing buffer solution by differential pulse voltammetry (DPV) within 1-5 min, wherein an oxidation peak potential of the L-Trp is 0.82 V; and testing the L-Trp with different concentrations, drawing a working standard curve, then detecting the L-Trp in the sample to be tested by a standard addition method, wherein the formaldehyde-containing buffer solution is a formaldehyde-containing phosphate buffer solution (PBS), and the formaldehyde-containing PBS has a pH value of 7.0 and a concentration of 0.010-0.10 M, and a concentration of formaldehyde in the formaldehyde-containing buffer solution is 0.02-0.2 M.

2. The method according to claim 1, wherein step a) preparing the surface carboxylated F-MWCNTs by the blending acidification method specifically comprises the following steps:
firstly, mixing F-MWCNTs with a mixed acid to obtain a second mixture, wherein the mixed acid consists of $H_2SO_4$ and $HNO_3$, a mass/volume ratio of the F-MWCNTs and the mixed acid is (0.15-0.25) g: (25-35) mL, and a volume ratio of the $H_2SO_4$ and the $HNO_3$ in the mixed acid is (2.5-3.5):1; after performing a third ultrasonic dispersion on the second mixture, refluxing in an oil bath under a stirring at 115-125° C. for 2.5-3.5 h to obtain a mixed solution;
then diluting the mixed solution with ultrapure water to obtain a diluted mixed solution, and centrifuging the diluted mixed solution with a high-speed centrifuge after cooling to obtain a first product;
finally, washing the first product with ethanol for three times and centrifuging the first product to obtain a second product, drying the second product into powder in an electric blast drying oven at 55-65° C. to obtain the surface carboxylated F-MWCNTs, and storing the surface carboxylated F-MWCNTs for later use.

3. The method according to claim 1, wherein step b) preparing the CuS NS specifically comprises the following steps:
firstly, adding $CuCl·2H_2O$ into a container containing a mixture of oleylamine and octylamine to obtain a first mixed solution, wherein a mass/volume ratio of the $CuCl·2H_2O$ to the mixture of oleylamine and octylamine is (0.15-0.25) g: (25-45) mL, a volume ratio of the oleylamine and the octylamine in the mixture of oleylamine and octylamine is 1:(1-2); heating the first mixed solution to 100° C. in an oil bath to obtain a first resulting solution, and then performing a first magnetic stirring under vacuum for 20-60 min to remove water and oxygen from the first resulting solution to obtain a first processed solution;
then raising a temperature of the first processed solution to 120-140° C. and keeping the first processed solution at 120-140° C. with a second magnetic stirring for 4.5-6.0 h to obtain a second resulting solution;
at the same time, preparing an ultrasonically homogeneous solution, wherein the ultrasonically homogeneous solution consists of sulfur powder and the mixture of oleylamine and octylamine, a mass/volume ratio of the sulfur powder and the mixture of oleylamine and octylamine is (0.1-0.2) g: (3-7) mL, a volume ratio of the oleylamine and the octylamine in the mixture of oleylamine and octylamine is 1:(1-2);
when the second resulting solution becomes transparent after heating for 4.5-6.0 h, injecting the ultrasonically homogeneous solution into the second resulting solution quickly to obtain a second mixed solution, heating the second mixed solution for 8-24 h;
finally, cooling the second mixed solution to room temperature, washing the second mixed solution with excess ethanol and centrifuging the second mixed solution to obtain a precipitate, and then drying the precipitate into powder in an electric blast drying oven at 55-65° C. to obtain the CuS NS, and storing the CuS NS in a refrigerator for later use.

4. The method according to claim 1, wherein a shape of the CuS NS is a hexagon with a side length of 10.46±0.65 nm and a thickness of 5.27±0.74 nm.

5. The method according to claim 1, wherein polishing the surface of the glassy carbon electrode in step (2) is to successively polish the surface of the glassy carbon electrode with 1.0 μm, 0.3 μm and 0.05 μm aluminum oxide powder.

6. The method according to claim 1, wherein a diameter of the glassy carbon electrode in step (2) is 3 mm, 5 μL of the F-MWCNT dispersed solution is coated on the polished surface of the glassy carbon electrode dropwise and dried, and 5 μL of the CuS NS—CS homogeneous solution is coated on the F-MWCNT-modified glassy carbon electrode.

7. The method according to claim 1, wherein in step (3), a pulse amplitude of the DPV is 0.05 V, a pulse width of the DPV is 0.2 s, a sampling width of the DPV is 0.02 and a pulse period of the DPV is 0.5 s.

8. The method according to claim 1, wherein a linear range of the L-Trp is $8.0×10^{-7}$-$6.0×10^{-5}$ mol/L, and a lower detection limit of the L-Trp is $4.6×10^{-8}$ mol/L.

9. A method of constructing a sensing platform for selectively detecting L-Trp, comprising applying the method according to claim 1 in constructing the sensing platform for selectively detecting the L-Trp, wherein the L-Trp is separated from L-tyrosine (L-Tyr) at an oxidation peak potential difference of the L-Trp and the L-Tyr, and the oxidation peak potential difference ranges from 0.12 to 0.24 V.

10. The method according to claim 9, wherein step a) preparing the surface carboxylated F-MWCNTs by the blending acidification method specifically comprises the following steps: firstly, mixing F-MWCNTs with a mixed acid to obtain a second mixture, wherein the mixed acid consists of $H_2SO_4$ and $HNO_3$, a mass/volume ratio of the F-MWCNTs and the mixed acid is (0.15-0.25) g: (25-35) mL, and a volume ratio of the $H_2SO_4$ and the $HNO_3$ in the mixed acid is (2.5-3.5):1; after performing a third ultrasonic dispersion on the second mixture, refluxing in an oil bath under a stirring at 115-125° C. for 2.5-3.5 h to obtain a mixed solution; then diluting the mixed solution with ultrapure water to obtain a diluted mixed solution, and centrifuging the diluted mixed solution with a high-speed centrifuge after cooling to obtain a first product; finally, washing the first product with ethanol for three times and centrifuging the first product to obtain a second product, drying the second product into powder in an electric blast drying oven at 55-65° C. to obtain the surface carboxylated F-MWCNTs, and storing the surface carboxylated F-MWCNTs for later use.

11. The method according to claim 9, wherein step b) preparing the CuS NS specifically comprises the following steps: firstly, adding CuCl into a container containing a mixture of oleylamine and octylamine to obtain a first mixed solution, wherein a mass/volume ratio of the CuCl to the mixture of oleylamine and octylamine is (0.15-0.25) g: (2545) mL, a volume ratio of the oleylamine and the octylamine in the mixture of oleylamine and octylamine is 1:(1-2); heating the first mixed solution to 100° C. in an oil bath to obtain a first resulting solution, and then performing a first magnetic stirring under vacuum for 20-60 min to remove water and oxygen from the first resulting solution to obtain a first processed solution; then raising a temperature of the first processed solution to 120-140° C. and keeping the first processed solution at 120-140° C. with a second magnetic stirring for 4.5-6.0 h to obtain a second resulting solution; at the same time, preparing an ultrasonically homogeneous solution, wherein the ultrasonically homogeneous solution consists of sulfur powder and the mixture of oleylamine and octylamine, a mass/volume ratio of the sulfur powder and the mixture of oleylamine and octylamine is (0.1-0.2) g: (3-7) mL, a volume ratio of the oleylamine and the octylamine in the mixture of oleylamine and octylamine is 1:(1-2); when the second resulting solution becomes transparent after heating for 4.5-6.0 h, injecting the ultrasonically homogeneous solution into the second resulting solution quickly to obtain a second mixed solution, heating the second mixed solution for 8-24 h; finally, cooling the second mixed solution to room temperature, washing the second mixed solution with excess ethanol and centrifuging the second mixed solution to obtain a precipitate, and then drying the precipitate into powder in an electric blast drying oven at 55-65° C. to obtain the CuS NS, and storing the CuS NS in a refrigerator for later use.

12. The method according to claim 9, wherein a shape of the CuS NS is a hexagon with a side length of 10.46±0.65 nm and a thickness of 5.27±0.74 nm.

13. The method according to claim 9, wherein polishing the surface of the glassy carbon electrode in step (2) is to successively polish the surface of the glassy carbon electrode with 1.0 μm, 0.3 μm and 0.05 μm aluminum oxide powder.

14. The method according to claim 9, wherein a diameter of the glassy carbon electrode in step (2) is 3 mm, 5 μL of the F-MWCNT dispersed solution is coated on the polished surface of the glassy carbon electrode dropwise and dried, and 5 μL of the CuS NS—CS homogeneous solution is coated on the F-MWCNT-modified glassy carbon electrode.

15. The method according to claim 9, wherein in step (3), a pulse amplitude of the DPV is 0.05 V, a pulse width of the DPV is 0.2 s, a sampling width of the DPV is 0.02 and a pulse period of the DPV is 0.5 s.

16. The method according to claim 9, wherein a linear range of the L-Trp is $8.0 \times 10^{-7}$-$6.0 \times 10^{-5}$ mol/L, and a lower detection limit of the L-Trp is $4.6 \times 10^{-8}$ mol/L.

\* \* \* \* \*